United States Patent
Waycuilis

(10) Patent No.: US 7,244,867 B2
(45) Date of Patent: Jul. 17, 2007

(54) PROCESS FOR CONVERTING GASEOUS ALKANES TO LIQUID HYDROCARBONS

(75) Inventor: John J. Waycuilis, Cypress, TX (US)

(73) Assignee: Marathon Oil Company, Houston, TX (US)

(*) Notice: Subject to any disclaimer, the term of this patent is extended or adjusted under 35 U.S.C. 154(b) by 65 days.

(21) Appl. No.: 10/826,885

(22) Filed: Apr. 16, 2004

(65) Prior Publication Data

US 2005/0234276 A1    Oct. 20, 2005

(51) Int. Cl.
  *C07C 1/00* (2006.01)
(52) U.S. Cl. .............. 585/408; 585/359; 585/469; 585/642; 585/733
(58) Field of Classification Search ............... 585/408, 585/359, 469, 642, 733
See application file for complete search history.

(56) References Cited

U.S. PATENT DOCUMENTS

| | | | |
|---|---|---|---|
| 2,168,260 A | 8/1939 | Heisel et al. | |
| 2,246,082 A | 6/1941 | Vaughan et al. | |
| 2,488,083 A | 11/1949 | Gorin et al. | |
| 2,677,598 A | 5/1954 | Crummett et al. | |
| 2,941,014 A | 6/1960 | Rothweiler et al. | |
| 3,172,915 A | 3/1965 | Borkowski et al. | |
| 3,246,043 A | 4/1966 | Rossett et al. | |
| 3,562,321 A | 2/1971 | Borkowski et al. | |
| 3,598,876 A | 8/1971 | Bloch | |
| 3,702,886 A | 11/1972 | Argauer et al. | |
| 3,876,715 A | 4/1975 | McNulty et al. | |
| 3,894,105 A | 7/1975 | Chang et al. | |
| 3,894,107 A | 7/1975 | Butter et al. | |
| 4,197,420 A | 4/1980 | Ferraris et al. | |
| 4,347,391 A | 8/1982 | Campbell | |
| 4,467,130 A | 8/1984 | Olah | |
| 4,489,210 A | 12/1984 | Judat et al. | |
| 4,513,092 A | 4/1985 | Chu et al. | |

(Continued)

FOREIGN PATENT DOCUMENTS

GB    474922 A    11/1937

(Continued)

OTHER PUBLICATIONS

Ivan Lorkovic et al "Alkan Oligomerization for the Production of Alkanes, Olefins, Alcohols, Ethers, Fuels, and Aromatics" pp. 1-6.*

(Continued)

*Primary Examiner*—Tam M. Nguyen
(74) *Attorney, Agent, or Firm*—Jack E. Ebel

(57) ABSTRACT

A process for converting gaseous alkanes to liquid hydrocarbons wherein a gaseous feed containing alkanes is reacted with a dry bromine vapor to form alkyl bromides and hydrobromic acid vapor. The mixture of alkyl bromides and hydrobromic acid are then reacted over a synthetic crystalline alumino-silicate catalyst, such as a ZSM-5 zeolite, at a temperature of from about 150° C. to about 400° C. so as to form higher molecular weight hydrocarbons and hydrobromic acid vapor. Hydrobromic acid vapor is removed from the higher molecular weight hydrocarbons. A portion of the propane and butane is removed from the higher molecular weight hydrocarbons and reacted with the mixture of alkyl bromides and hydrobromic acid over the synthetic crystalline alumino-silicate catalyst to form $C_5+$ hydrocarbons.

28 Claims, 6 Drawing Sheets

U.S. PATENT DOCUMENTS

| | | | |
|---|---|---|---|
| 4,523,040 | A | 6/1985 | Olah |
| 4,652,688 | A | 3/1987 | Brophy et al. |
| 4,655,893 | A | 4/1987 | Beale |
| 4,665,270 | A | 5/1987 | Brophy et al. |
| 4,748,013 | A | 5/1988 | Saito et al. |
| 4,769,504 | A | 9/1988 | Noceti et al. |
| 4,795,843 | A | 1/1989 | Imai et al. |
| 4,804,797 | A | 2/1989 | Minet et al. |
| 4,973,786 | A | 11/1990 | Karra |
| 5,001,293 | A | 3/1991 | Nubel et al. |
| 5,157,189 | A | 10/1992 | Karra |
| 5,243,098 | A | 9/1993 | Miller et al. |
| 5,276,240 | A | 1/1994 | Timmons et al. |
| 5,334,777 | A | 8/1994 | Miller et al. |
| 5,705,728 | A | 1/1998 | Viswanathan et al. |
| 5,969,195 | A | 10/1999 | Stabel et al. |
| 5,998,679 | A | 12/1999 | Miller |
| 6,403,840 | B1 | 6/2002 | Zhou et al. |
| 6,452,058 | B1 | 9/2002 | Schweizer et al. |
| 6,462,243 | B1 | 10/2002 | Zhou et al. |
| 6,465,696 | B1 | 10/2002 | Zhou et al. |
| 6,465,699 | B1 | 10/2002 | Grosso |
| 6,472,572 | B1 | 10/2002 | Zhou et al. |
| 6,486,368 | B1 | 11/2002 | Zhou et al. |
| 6,525,230 | B2 | 2/2003 | Grosso |
| 6,713,655 | B2 | 3/2004 | Yilmaz et al. |
| 2003/0120121 | A1 | 6/2003 | Sherman et al. |
| 2003/0125589 | A1 | 7/2003 | Grosso |
| 2003/0166973 | A1 | 9/2003 | Zhou et al. |
| 2005/0038310 | A1 | 2/2005 | Lorkovic et al. |
| 2005/0171393 | A1 | 8/2005 | Lorkovic |

FOREIGN PATENT DOCUMENTS

| | | |
|---|---|---|
| GB | 883256 A | 11/1961 |
| GB | 1104294 | 2/1968 |
| GB | 2120249 A | 11/1983 |

OTHER PUBLICATIONS

JLM Technology LTD.; "The Miller GLS Technology for Conversion of Light Hydrocarbons to Alcohols"; New Science for the Benefit of Humanity; May 31, 2005; pp. 1-10.

Jaumain, Denis and Su, Bao-Lian; "Direct Catalytic Conversion of Chloromethane to Higher Hydrocarbons . . . "; 2000; pp. 1607-1612; Studies in Surface Science and Catalysis 130.

Taylor, Charles E.; "Conversion of Substituted Methanes Over ZSM-Catalysts"; 2000; pp. 3633-3638; Studies in Surface Science and Catalysis 130; Elsevier Science B.V.

ZSM-5 Catalyst; http://chemelab.ucsd.edu/methanol/memos/ZSM-5.html; Nov. 6, 2003; p. 1.

Final Report; "Abstract"; http://chemelab.ucsd.edu/methanol/memos/final.html; May 9, 2004; pp. 1-7.

Driscoll, Daniel J.; "Direct Methane Conversion"; Federal Energy Technology Center, U.S. Dept. of Energy; M970779; pp. 1-10.

Olah et al.; "Selective Monohalogenation of Methane Over Supported . . . "; J. American Chemical Society 1985, vol. 107; 0002-7863/85/1507-7097$01.50/0; pp. 7097-7105.

Murray et al.; "Conversion of Methyl Halides to Hydrocarbons on Basic Zeolites: A Discovery by in Situ NMR"; J. Am. Chem. Soc. 1993, vol. 115; pp. 4732-4741.

Lorkovic et al., "A novel integrated process for the functionalization of methane and ethane: bromine as mediator", Catalysis Today, 98(2004) pp. 317-322.

Lorkovic et al., "C1 oxidative coupling via bromine activation and tandem catalytic condensation over CaO/zeolite composites II", Catalysis Today 98 (2004) pp. 589-594.

Olah et al.; "Antimony Pentafluoride/Graphite Catalyzed Oxidative Conversion of . . . "; J. Org. Chem. 1990, 55; 1990 American Chemical Society; pp. 4289-4293.

Taylor et al.; "Direct Conversion of Methane to Liquid Hydrocarbons . . . "; Methane Conversion; 1988 Elsevier Science Publishers B.V. Amsterdam; pp. 483-489.

Chang et al.; "The Conversion of Methanol and Other O-Compounds to Hydrocarbons over Zeolite Catalysts"; Journal of Catalysis 47; 1977; Academic Press, Inc.; pp. 249-259.

Zhou et al.; "An Integrated Process for Partial Oxidation of Alkanes"; Chem. Commun. 2003; The Royal Society of Chemistry; pp. 2294-2295.

Sun et al.; "A General Integrated Process for Synthesizing Olefin Oxides"; Chem. Commun. 2004; The Royal Society of Chemistry; pp. 2100-2101.

Lorkovic et al.; "C1 Oxidative Coupling via Bromine Activation and Tandem Catalytic Condensation and Neutralization over CaO/zeolite . . . "; Catalysis Today 98 2004; pp. 589-594.

Yilmaz et al.; "Bromine Mediated Partial Oxidation of Ethane over Nanostructured Zirconia Supported . . . "; Microporous and Mesoporous Materials 79 2005; Elsevier; pp. 205-214.

Taylor; "PETC's On-Site Natural Gas Conversion Efforts"; Preprints of the Fuel Division, 208th National Meeting of the American Chemical Society, 39(4); 1994; pp. 1228-1232.

U.S. Appl. No. 60/487,364, Lorkovic et al.

Ione et al.; "Syntheses of Hydrocarbons from Compounds . . . "; Solid Fuel Chemistry (Khimiya Tverdogo Topliva); 1982; pp. 29-43; vol. 16, No. 6; Allerton Press, Inc.

Olah et al.; "Hydrocarbons Through Methane Derivatives"; Hydrocarbon Chemistry; 1995; pp. 89-90; John Wiley & Sons, Inc.

* cited by examiner

C6+ Condensed Product Sample

PROCESS FOR CONVERTING GASEOUS ALKANES TO LIQUID HYDROCARBONS

BACKGROUND OF THE INVENTION

1. Field of the Invention

The present invention relates to a process for converting lower molecular weight, gaseous alkanes to liquid hydrocarbons useful for the production of fuels, and more particularly, to a process wherein a gas containing lower molecular weight alkanes is reacted with a dry bromine vapor to form alkyl bromides and hydrobromic acid which in turn are reacted over a crystalline alumino-silicate catalyst to form liquid hydrocarbons.

2. Description of Related Art

Natural gas which is primarily composed of methane and other light alkanes has been discovered in large quantities throughout the world. Many of the locales in which natural gas has been discovered are far from populated regions which have significant gas pipeline infrastructure or market demand for natural gas. Due to the low density of natural gas, transportation thereof in gaseous form by pipeline or as compressed gas in vessels is expensive. Accordingly, practical and economic limits exist to the distance over which natural gas may be transported in gaseous form exist. Cryogenic liquefaction of natural gas (LNG) is often used to more economically transport natural gas over large distances. However, this LNG process is expensive and there are limited regasification facilities in only a few countries that are equipped to import LNG.

Another use of methane found in natural gas is as feed to processes for the production of methanol. Methanol is made commercially via conversion of methane to synthesis gas (CO and $H_2$) at high temperatures (approximately 1000° C.) followed by synthesis at high pressures (approximately 100 atmospheres). There are several types of technologies for the production of synthesis gas (CO and $H_2$) from methane. Among these are steam-methane reforming (SMR), partial oxidation (POX), autothermal reforming (ATR), gas-heated reforming (GHR), and various combinations thereof. SMR and GHR operate at high pressures and temperatures, generally in excess of 600° C., and require expensive furnaces or reactors containing special heat and corrosion-resistant alloy tubes filled with expensive reforming catalyst. POX and ATR processes operate at high pressures and even higher temperatures, generally in excess of 1000° C. As there are no known practical metals or alloys that can operate at these temperatures, complex and costly refractory-lined reactors and high-pressure waste-heat boilers to quench & cool the synthesis gas effluent are required. Also, significant capital cost and large amounts of power are required for compression of oxygen or air to these high-pressure processes. Thus, due to the high temperatures and pressures involved, synthesis gas technology is expensive, resulting in a high cost methanol product which limits higher-value uses thereof, such as for chemical feedstocks and solvents. Furthermore production of synthesis gas is thermodynamically and chemically inefficient, producing large excesses of waste heat and unwanted carbon dioxide, which tends to lower the conversion efficiency of the overall process. Fischer-Tropsch Gas-to-Liquids (GTL) technology can also be used to convert synthesis gas to heavier liquid hydrocarbons, however investment cost for this process is even higher. In each case, the production of synthesis gas represents a large fraction of the capital costs for these methane conversion processes.

Numerous alternatives to the conventional production of synthesis gas as a route to methanol or synthetic liquid hydrocarbons have been proposed. However, to date, none of these alternatives has attained commercial status for various reasons. Some of the previous alternative prior-art methods, such as disclosed in U.S. Pat. Nos. 5,243,098 or 5,334,777 to Miller, teach reacting a lower alkane, such as methane, with a metallic halide to form a metalous halide and hydrohalic acid which are in turn reduced with magnesium oxide to form the corresponding alkanol. However, halogenation of methane using chlorine as the preferred halogen results in poor selectivity to the monomethyl halide ($CH_3Cl$), resulting in unwanted by-products such as $CH_2Cl_2$ and $CHCl_3$ which are difficult to convert or require severe limitation of conversion per pass and hence very high recycle rates. Furthermore, these processes require movement and fluidization of solid metal salts and/or oxides which requires significant power, causes erosion of equipment and generation of fine dust which must be recovered and recycled.

Other prior art processes propose the catalytic chlorination or bromination of methane as an alternative to generation of synthesis gas (CO and $H_2$). To improve the selectivity of a methane halogenation step in an overall process for the production of methanol, U.S. Pat. No. 5,998,679 to Miller teaches the use of bromine, generated by thermal decomposition of a metal bromide, to brominate alkanes in the presence of excess alkanes, which results in improved selectivity to mono-halogenated intermediates such as methyl bromide. To avoid the drawbacks of utilizing fluidized beds of moving solids, the process utilizes a liquid mixture of metal chloride hydrates and metal bromides. Processes described in U.S. Pat. No. 6,462,243 B1, U.S. Pat. No. 6,472,572 B1, and U.S. Pat. No. 6,525,230 to Grosso are capable of attaining higher selectivity to mono-halogenated intermediates by the use of catalytic bromination. The resulting alkyl bromides intermediates such as methyl bromide, are further converted to the corresponding alcohols and ethers, by reaction with metal oxides in circulating beds of moving solids, with the drawbacks that beds of moving solids entail as described above. Another embodiment of U.S. Pat. No. 6,525,230 avoids the drawbacks of moving beds by utilizing a zoned reactor vessel containing a fixed bed of metal oxide/metal bromide that is operated cyclically in four steps. Additional drawbacks to the processes described in these patents are the simultaneous feeding of hydrocarbon gas and oxygen or air to a reactor vessel increasing the potential of an explosive condition occurring within the equipment in the event of an unanticipated process upset or mechanical failure. Also, these processes tend to produce substantial quantities of dimethylether (DME) along with any alcohol. While DME is a promising potential diesel engine fuel substitute, as of yet, there currently exists no substantial market for DME, and hence an expensive additional catalytic process conversion step would be required to convert DME into a currently marketable product. Other processes have been proposed which circumvent the need for production of synthesis gas, such as U.S. Pat. Nos. 4,655,893 and 4,467,130 to Olah in which methane is catalytically condensed into gasoline-range hydrocarbons via catalytic condensation using superacid catalysts. However, none of these earlier alternative approaches have resulted in commercial processes.

It is known that substituted alkanes, in particular methanol, can be converted to olefins and gasoline boiling-range hydrocarbons over various forms of crystalline alumino-silicates also known as zeolites. In the Methanol to Gasoline (MTG) process, a shape selective zeolite catalyst, ZSM-5, is used to convert methanol to gasoline. Coal or methane gas can thus be converted to methanol using conventional technology and subsequently converted to gasoline. However due to the high cost of methanol production, and at current or projected prices for gasoline, the MTG process is not considered economically viable. Thus, a need exists for an economic process for the for the conversion of methane and other alkanes found in natural gas to useful liquid hydrocarbon products which, due to their higher density and value, are more economically transported thereby significantly aiding development of remote natural gas reserves. A further need exists for a process for converting alkanes present in natural gas which is relatively inexpensive, safe and simple in operation.

SUMMARY OF THE INVENTION

To achieve the foregoing and other objects, and in accordance with the purposes of the present invention, as embodied and broadly described herein, one characterization of the present invention is a process for converting gaseous alkanes to liquid hydrocarbons. A gaseous feed having lower molecular weight alkanes is reacted with bromine vapor to form alkyl bromides and hydrobromic acid which in turn are reacted in the presence of a synthetic crystalline aluminosilicate catalyst and at a temperature sufficient to form higher molecular weight hydrocarbons and hydrobromic acid vapor.

In another characterization of the present invention, a process is provided for converting gaseous lower molecular weight alkanes to liquid hydrocarbons wherein a gaseous feed containing lower molecular weight alkanes is reacted with bromine vapor to form alkyl bromides and hydrobromic acid. The alkyl bromides and hydrobromic acid are reacted in the presence of a synthetic crystalline aluminosilicate catalyst to form higher molecular weight hydrocarbons and hydrobromic acid vapor. Bromine is recovered from the hydrobromic acid vapor.

BRIEF DESCRIPTION OF THE DRAWINGS

The accompanying drawings, which are incorporated in and form a part of the specification, illustrate the embodiments of the present invention and, together with the description, serve to explain the principles of the invention.

In the drawings.

DETAILED DESCRIPTION OF THE PREFERRED EMBODIMENTS

Figure 2:
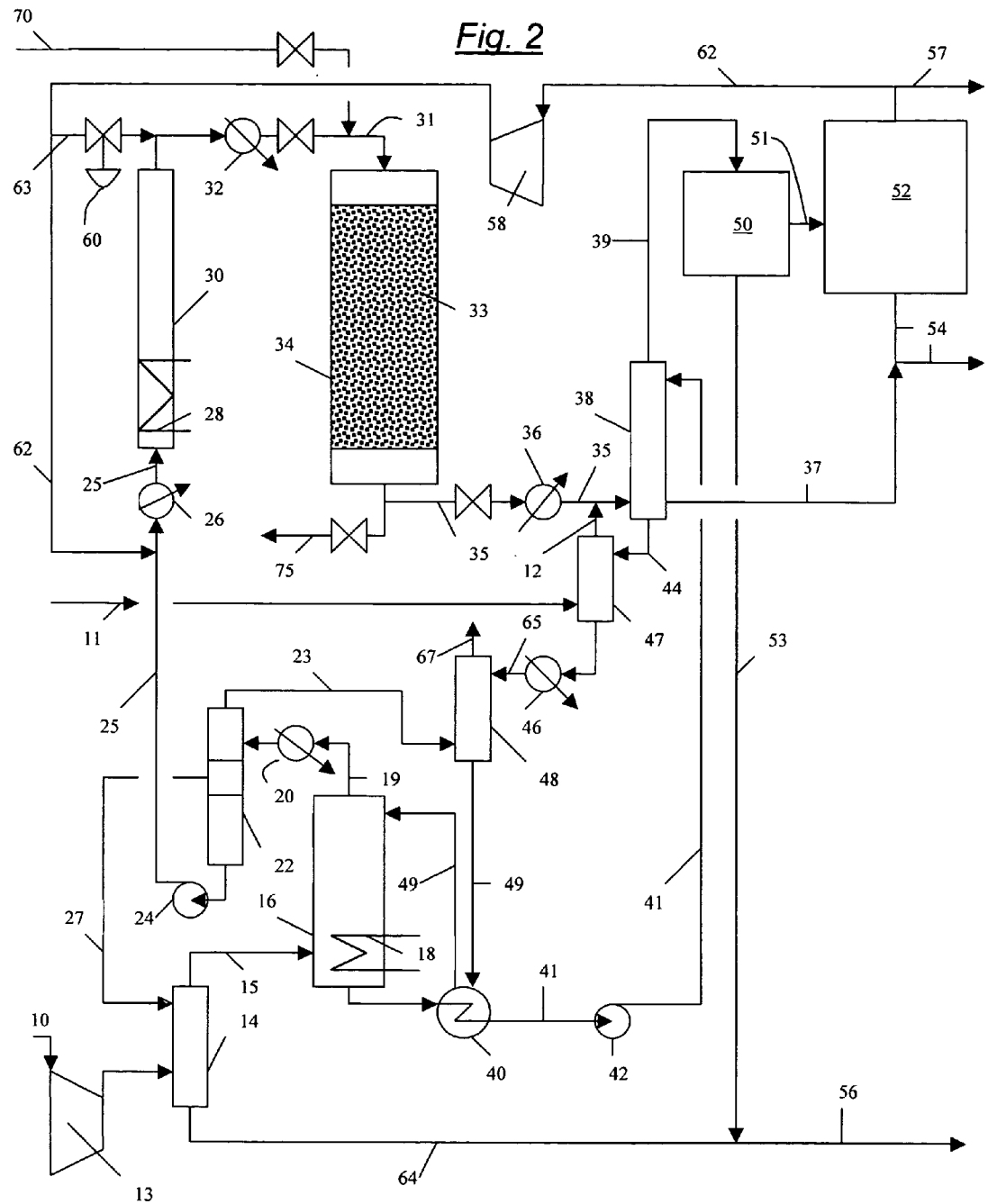
FIG. 2 is a schematic view of one embodiment of the process of the present invention.
Figure 3:
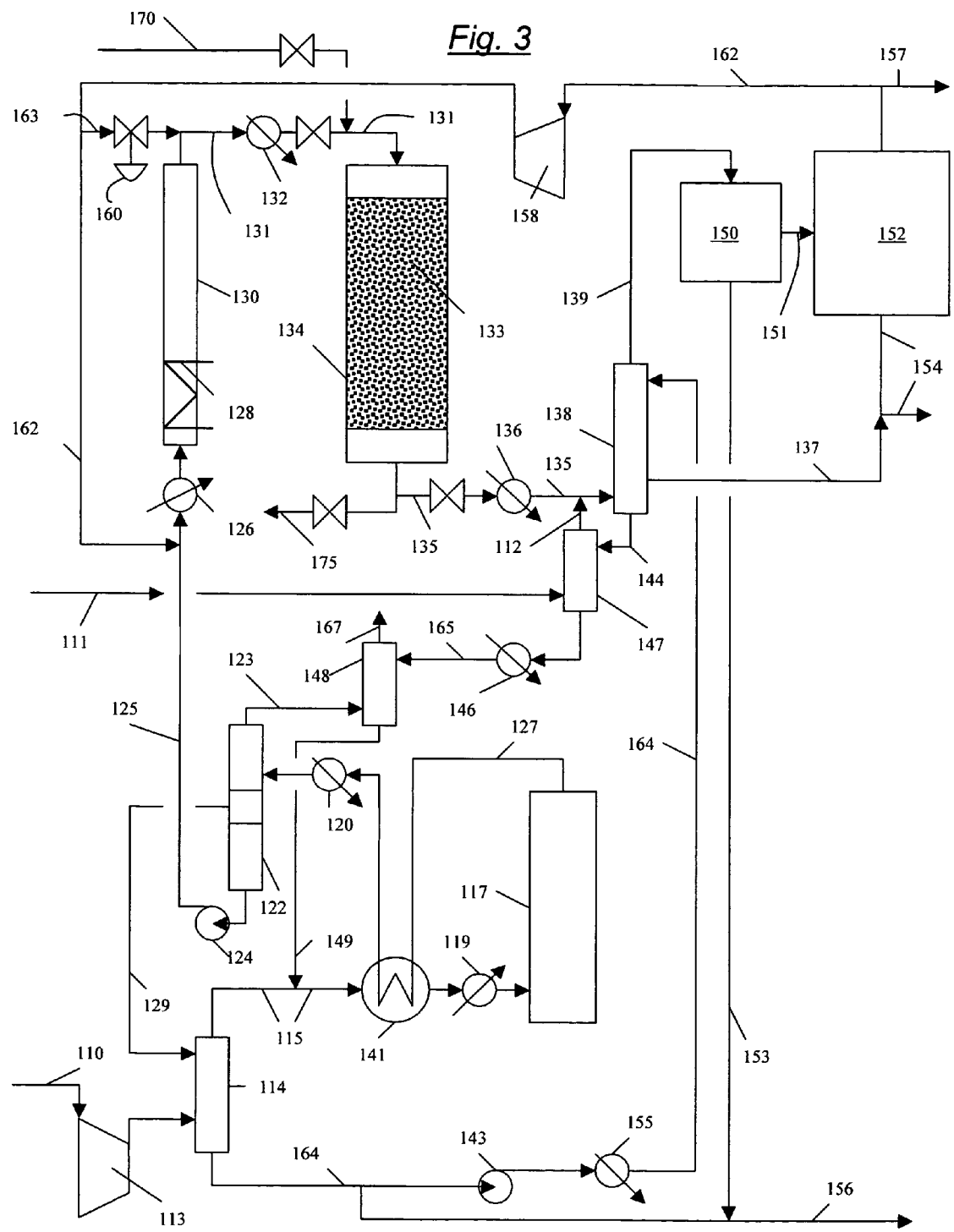
FIG. 3 is a schematic view of another embodiment of process of the present invention.

As utilized throughout this description, the term "lower molecular weight alkanes" refers to methane, ethane, propane, butane, pentane or mixtures thereof. As also utilized throughout this description, "alkyl bromides" refers to mono, di, and tri brominated alkanes. Also, the feed gas in lines 11 and 111 in the embodiments of the process of the present invention as illustrated in FIGS. 2 and 3, respectively, is preferably natural gas which may be treated to remove sulfur compounds and carbon dioxide. In any event, it is important to note that small amounts of carbon dioxide, e.g. less than about 2 mol %, can be tolerated in the feed gas to the process of the present invention.

Figure 1:
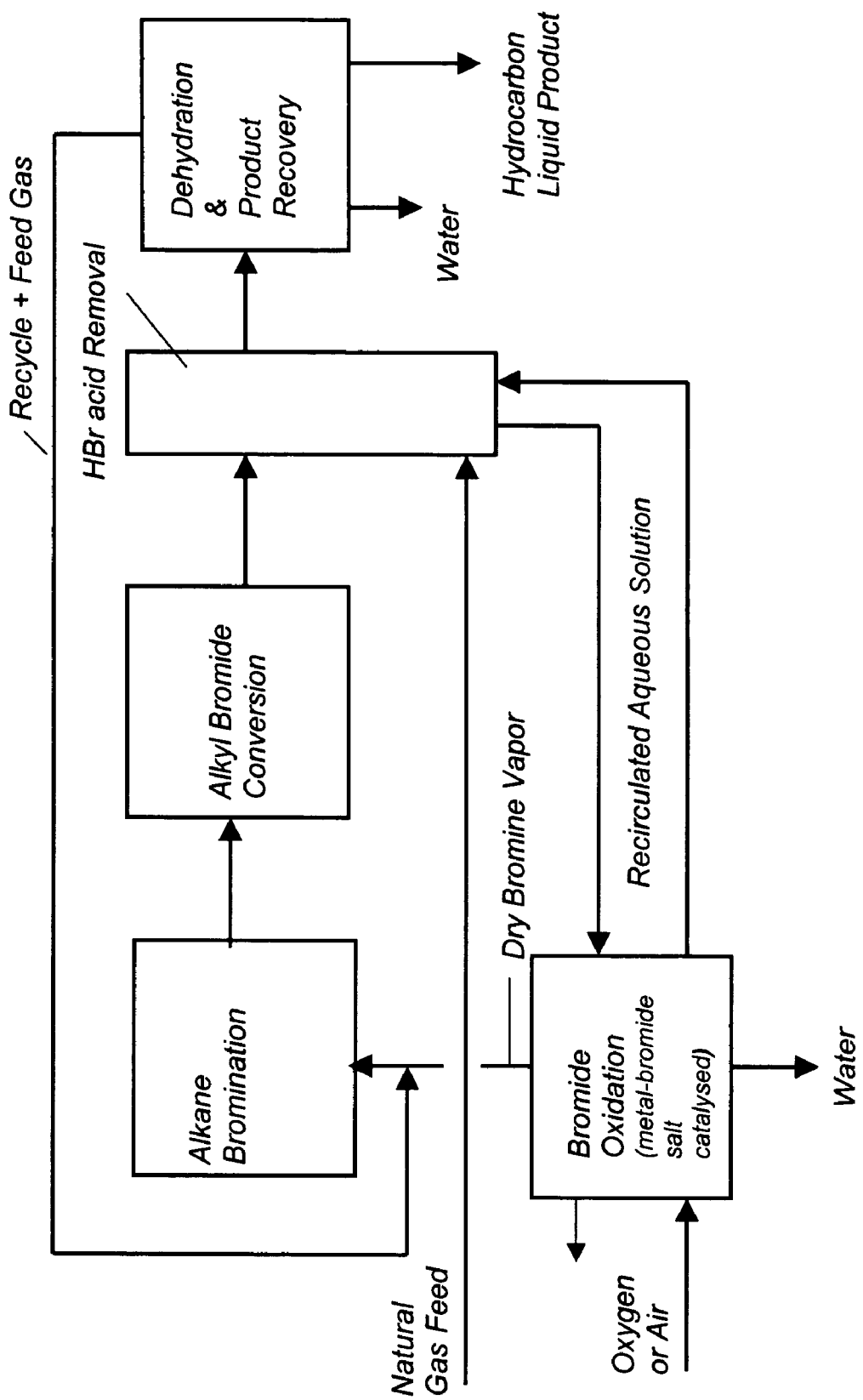
FIG. 1 is a simplified block flow diagram of the process of the present invention.

A block flow diagram generally depicting the process of the present invention is illustrated in FIG. 1, while specific embodiments of the process of the present invention are illustrated in FIGS. 2 and 3. Referring to FIG. 2, a gas stream containing lower molecular weight alkanes, comprised of a mixture of a feed gas plus a recycled gas stream at a pressure in the range of about 1 bar to about 30 bar, is transported or conveyed via line, pipe or conduit 62, mixed with dry bromine liquid transported via line 25 and pump 24, and passed to heat exchanger 26 wherein the liquid bromine is vaporized. The mixture of lower molecular weight alkanes and dry bromine vapor is fed to reactor 30. Preferably, the molar ratio of lower molecular weight alkanes to dry bromine vapor in the mixture introduced into reactor 30 is in excess of 2.5:1. Reactor 30 has an inlet pre-heater zone 28 which heats the mixture to a reaction initiation temperature in the range of about 250° C. to about 400° C.

In first reactor 30, the lower molecular weight alkanes are reacted exothermically with dry bromine vapor at a relatively low temperature in the range of about 250° C. to about 600° C., and at a pressure in the range of about 1 bar to about 30 bar to produce gaseous alkyl bromides and hydrobromic acid vapors. The upper limit of the operating temperature range is greater than the upper limit of the reaction initiation temperature range to which the feed mixture is heated due to the exothermic nature of the bromination reaction. In the case of methane, the formation of methyl bromide occurs in accordance with the following general reaction:

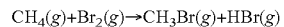

$$CH_4(g)+Br_2(g) \rightarrow CH_3Br(g)+HBr(g)$$

This reaction occurs with a significantly high degree of selectivity to methyl bromide. For example, in the case of bromination of methane with a methane to bromine ratio of about 4.5:1 selectivity to the mono-halogenated methyl bromide is in the range of 90 to 95%. Small amounts of dibromomethane and tribromomethane are also formed in the bromination reaction. Higher alkanes, such as ethane, propane and butane, are also readily bromoninated resulting in mono and multiple brominated species. If an alkane to bromine ratio of significantly less than about 2.5 to 1 is utilized, selectivity to methyl bromide substantially lower than 90% occurs and significant formation of undesirable carbon soot is observed. It has also been shown that other alkanes such as ethane and propane which may be present in the feed gas to the bromination reactor are readily brominated to form ethyl bromides and propyl bromides. Further, the dry bromine vapor that is feed into first reactor 30 is substantially water-free. Applicant has discovered that elimination of substantially all water vapor from the bromination step in first reactor 30 substantially eliminates the formation of unwanted carbon dioxide thereby increasing the selectivity of alkane bromination to alkyl bromides and eliminating the large amount of waste heat generated in the formation of carbon dioxide from alkanes.

The effluent that contains alkyl bromides and hydrobromic acid is withdrawn from the first reactor via line 31 and is partially cooled to a temperature in the range of about 150° C. to about 350° C. in heat exchanger 32 before flowing to a second reactor 34. In second reactor 34, the alkyl bromides are reacted exothermically at a temperature range of from about 150° C. to about 400° C., and a pressure in the range of about 1 to 30 bar, over a fixed bed 33 of crystalline alumino-silicate catalyst, preferably a zeolite catalyst, and most preferably a ZSM-5 zeolite catalyst. Although the zeolite catalyst is preferably used in the sodium or magnesium form, the zeolite may also be modified by ion exchange with other alkali metal cations, such as Li, K or Cs, with alkali-earth metal cations, such as Mg, Ca, Sr or Ba, or with transition metal cations, such as Ni, Mn, V, W. Other zeolite catalysts having varying pore sizes and acidities, which are synthesized by varying the alumina-to-silica ratio may be used in the second reactor 34 as will be evident to a skilled artisan. In this reactor, the alkyl bromides are oligimerized to produce a mixture of higher molecular weight hydrocarbon products, primarily $C_3$, $C_4$ and $C_5+$ gasoline-range and heavier hydrocarbon fractions, and additional hydrobromic acid vapor.

The temperature at which the second reactor 34 is operated is an important parameter in determining the selectivity of the oligimerization reaction to various higher molecular weight liquid hydrocarbon products. It is preferred to operated second reactor 34 at a temperature within the range of about 150° to 400°. Temperatures above about 300° C. in the second reactor result in increased yields of light hydrocarbons, such as undesirable methane, whereas lower temperatures increase yields of heavier molecular weight hydrocarbon products. At the low end of the temperature range, with methyl bromide reacting over ZSM-5 zeolite at temperatures as low as 150° C. significant methyl bromide conversion on the order of 20% is noted, with a high selectivity towards $C_5+$ products. Also it is noted that methyl bromide appears to be more reactive over a lower temperature range relative to methyl chloride or other substituted methyl compounds such as methanol. Notably, in the case of the alkyl bromide reaction over the preferred zeolite ZSM-5 catalyst, cyclization reactions also occur such that the $C_7+$ fractions are composed primarily of substituted aromatics. At increasing temperatures approaching 300° C., methyl bromide conversion increases towards 90% or greater, however selectivity towards $C_5+$ products decreases and selectivity towards lighter products, particularly undesirable methane, increases. Surprisingly, very little ethane or $C_2$,-$C_3$ olefins are formed. At temperatures above about 425° C. almost complete conversion of methyl bromide to methane occurs. As a byproduct of the reaction, a small amount of carbon will build up on the catalyst over time during operation, causing a decline in catalyst activity over a range of several hundred hours, depending on the reaction conditions. It is believed that higher reaction temperatures favor the formation of carbon or coke and hence the rate of deactivation of the catalyst. Conversely, temperatures at the lower end of the range may also contribute to coking due to a reduced rate of adsorption of products. Hence, operating temperatures within the range of about 150° C. to 400° C., but preferably in the range of about 250° C. to about 350° C. in the second reactor 34 balance increased selectivity of the desired $C_5+$ products and lower rates of deactivation due to carbon formation, against higher conversion per pass, which minimizes the quantity of catalyst, recycle rates and equipment size required.

The catalyst may be periodically regenerated in situ, by isolating reactor 34 from the normal process flow, purging with an inert gas via line 70 at a pressure in a range from about 1 to about 5 bar at an elevated temperature in the range of about 400° C. to about 600° C. to remove unreacted material adsorbed on the catalyst insofar as is practical, and then subsequently oxidizing the deposited carbon to $CO_2$ by addition of air to reactor 34 via line 70 at a pressure in the range of about 1 bar to about 5 bar at an elevated temperature in the range of about 400° C. to about 600° C. Carbon dioxide and residual air is vented from reactor 34 via line 75 during the regeneration period.

The effluent which comprises the higher molecular weight hydrocarbon products and hydrobromic acid is withdrawn from the second reactor 34 via line 35 and is cooled to a temperature in the range of 0° C. to about 100° C. in exchanger 36 and combined with vapor effluent in line 12 from hydrocarbon stripper 47, which contains feed gas and residual hydrocarbon products stripped-out by contact with the feed gas in hydrocarbon stripper 47. The combined vapor mixture is passed to a scrubber 38 and contacted with an aqueous partially-oxidized metal bromide salt solution containing metal hydroxide and/or metal oxy-bromide species, that is transported to scrubber 38 via line 41. The preferred metal of the bromide salt is Cu(II), Zn(II) or Fe(III) as these are less expensive and readily oxidize at lower temperatures in the range of 120° C. to 180° C., allowing the use of fluorpolymer-lined equipment; although Co(II), Ni(II), Mn(II) or other transition-metals which form oxidizable bromide salts may be used in the process of the present invention. Alternatively, alkaline-earth metals which also form oxidizable bromide salts, such as Ca (II) or Mg(II) may be used. Any liquid hydrocarbon product condensed in scrubber 38 may be skimmed and withdrawn in line 37 and added to liquid hydrocarbon product exiting the product recovery unit 52 in line 54. Hydrobromic acid is dissolved in the aqueous solution and neutralized by the metal hydroxide and or metal oxy-bromide species to yield metal bromide salt in solution and water which is removed from the scrubber 38 via line 44.

The residual vapor phase containing the higher molecular weight hydrocarbon products that is removed as effluent from the scrubber 38 is forwarded via line 39 to dehydrator 50 to remove substantially all water via line 53 from the vapor stream. The water is then removed from the dehydrator 50 via line 53. The dried vapor stream containing the higher molecular weight hydrocarbon products is further passed via line 51 to product recovery unit 52 to recover propane and butane as desired, but primarily the $C_5+$ fraction as a liquid product in line 54. Any conventional method of dehydration and liquids recovery, such as solid-bed dessicant adsorption followed by refrigerated condensation, cryogenic expansion, or circulating absorption oil, as used to process natural gas or refinery gas streaims, as will be evident to a skilled artisan, may be employed in the process of the present invention. The residual vapor effluent from product recovery unit 52 is then split into a purge stream 57 which may be utilized as fuel for the process and a recycled residual vapor which is compressed via compressor 58. The recycled residual vapor discharged from compressor 58 is split into two fractions. A first fraction that is equal to at least 2.5 times the feed gas molar volume is transported via line 62 and is combined with dry liquid bromine conveyed by pump 24, heated in exchanger 26 to vaporize the bromine and fed into first reactor 30. The second fraction is drawn off of line 62 via line 63 and is regulated by control valve 60, at a rate sufficient to dilute the alkyl bromide concentration to reactor 34 and absorb the heat of reaction such that reactor 34 is maintained at the selected operating temperature, preferably in the range of about 250° C. to about 350° C. in order to optimize conversion versus selectivity and to minimize the rate of catalyst deactivation due to the deposition of carbon. Thus, the dilution provided by the recycled vapor effluent permits selectivity of bromination in the first reactor 30 to be controlled in addition to moderating the temperature in second reactor 34.

Water containing metal bromide salt in solution which is removed from scrubber 38 via line 44 is passed to hydrocarbon stripper 47 wherein residual dissolved hydrocarbons are stripped from the aqueous phase by contact with incoming feed gas transported via line 11. The stripped aqueous solution is transported from hydrocarbon stripper 47 via line 65 and is cooled to a temperature in the range of about 0° C. to about 70° C. in heat exchanger 46 and then passed to absorber 48 in which residual bromine is recovered from vent stream in line 67. The aqueous solution effluent from scrubber 48 is transported via line 49 to a heat exchanger 40 to be preheated to a temperature in the range of about 100° C. to about 600° C., and most preferably in the range of about 120° C. to about 180° C. and passed to third reactor 16. Oxygen or air is delivered via line 10 by blower or compressor 13 at a pressure in the range of about ambient to about 5 bar to bromine stripper 14 to strip residual bromine from water which is removed from stripper 14 in line 64 and is combined with water stream 53 from dehydrator 50 to form water effluent stream in line 56 which is removed from the process. The oxygen or air leaving bromine stripper 14 is fed via line 15 to reactor 16 which operates at a pressure in the range of about ambient to about 5 bar and at a temperature in the range of about 100° C. to about 600° C., but most preferably in the range of about 120° C. to about 180° C. so as to oxidize an aqueous metal bromide salt solution to yield elemental bromine and metal hydroxide and or metal oxy-bromide species. As stated above, although Co(II), Ni(II), Mn(II) or other transition-metals which form oxidizable bromide salts can be used, the preferred metal of the bromide salt is Cu(II), Zn(II) or Fe(III) as these are less expensive and readily oxidize at lower temperatures in the range of about 120° C. to about 180° C., allowing the use of fluorpolymer-lined equipment. Alternatively, alkaline-earth metals which also form oxidizable bromide salts, such as Ca (II) or Mg(II) could be used.

Hydrobromic acid reacts with the metal hydroxide or metal oxy-bromide species so formed to once again yield the metal bromide salt and water. Heat exchanger 18 in reactor 16 supplies heat to vaporize water and bromine. Thus, the overall reactions result in the net oxidation of hydrobromic acid produced in first reactor 30 and second reactor 34 to elemental bromine and steam in the liquid phase catalyzed by the metal bromide/metal hydroxide operating in a catalytic cycle. In the case of the metal bromide being Cu(II) $Br_2$, the reactions are believed to be:

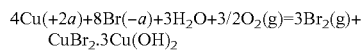

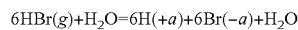

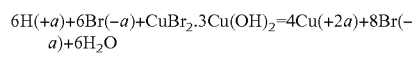

The elemental bromine and water and any residual oxygen or nitrogen (if air is utilized as the oxidant) leaving as vapor from the outlet of third reactor 16 via line 19, are cooled in condenser 20 at a temperature in the range of about 0° C. to about 70° C. and a pressure in the range of about ambient to 5 bar to condense the bromine and water and passed to three-phase separator 22. In three-phase separator 22, since liquid water has a limited solubility for bromine, on the order of about 3% by weight, any additional bromine which is condensed forms a separate, denser liquid bromine phase. The liquid bromine phase, however, has a notably lower solubility for water, on the order of less than 0.1%. Thus a substantially dry bromine vapor can be easily obtained by condensing liquid bromine and water, decanting water by simple physical separation and subsequently re-vaporizing liquid bromine.

Liquid bromine is pumped in line 25 from three-phase separator 22 via pump 24 to a pressure sufficient to mix with vapor stream 62. Thus bromine is recovered and recycled within the process. The residual oxygen or nitrogen and any residual bromine vapor which is not condensed exits three-phase separator 22 and is passed via line 23 to bromine scrubber 48, wherein residual bromine is recovered by solution into and by reaction with reduced metal bromides in the aqueous metal bromide solution stream 65. Water is removed from separator 22 via line 27 and introduced into stripper 14.

In another embodiment of the invention, referring to FIG. 3, a gas stream containing lower molecular weight alkanes, comprised of mixture of a feed gas plus a recycled gas stream at a pressure in the range of about 1 bar to about 30 bar, is transported or conveyed via line, pipe or conduit 162, mixed with dry bromine liquid transported via pump 124 and passed to heat exchanger 126 wherein the liquid bromine is vaporized. The mixture of lower molecular weight alkanes and dry bromine vapor is fed to reactor 130. Preferably, the molar ratio of lower molecular weight alkanes to dry bromine vapor in the mixture introduced into reactor 130 is in excess of 2.5:1. Reactor 130 has an inlet pre-heater zone 128 which heats the mixture to a reaction initiation temperature in the range of 250° C. to 400° C. In first reactor 130, the lower molecular weight alkanes are reacted exothermically with dry bromine vapor at a relatively low temperature in the range of 250° C. to 600° C., and at a pressure in the range of about 1 bar to about 30 bar to produce gaseous alkyl bromides and hydrobromic acid vapors. The upper limit of the operating temperature range is greater than the upper limit of the reaction initiation temperature range to which the feed mixture is heated due to the exothermic nature of the bromination reaction. In the case of methane, the formation of methyl bromide occurs in accordance with the following general reaction:

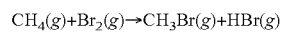

This reaction occurs with a significantly high degree of selectivity to methyl bromide. For example, in the case of bromine reacting with a molar excess of methane at a methane to bromine ratio of 4.5:1, selectivity to the mono-halogenated methyl bromide is in the range of 90 to 95%. Small amounts of dibromomethane and tribromomethane are also formed in the bromination reaction. Higher alkanes, such as ethane, propane and butane, are also readily brominated resulting in mono and multiple brominated species. If an alkane to bromine ratio of significantly less than 2.5 to 1 is utilized, selectivity to methyl bromide substantially lower than 90% occurs and significant formation of undesirable carbon soot is observed. It has also been shown that other alkanes such as ethane and propane which may be present in the feed gas to the bromination are readily brominated to form ethyl bromides and propyl bromides. Further, the dry bromine vapor that is feed into first reactor 130 is substantially water-free. Applicant has discovered that elimination of substantially all water vapor from the bromination step in first reactor 130 substantially eliminates the formation of unwanted carbon dioxide thereby increasing the selectivity of alkane bromination to alkyl bromides and eliminating the large amount of waste heat generated in the formation of carbon dioxide from alkanes.

The effluent that contains alkyl bromides and hydrobromic acid is withdrawn from the first reactor 130 via line 131 and is partially cooled to a temperature in the range of about 150° C. to 350° C. in heat exchanger 132 before flowing to a second reactor 134. In second reactor 134, the alkyl bromides are reacted exothermically at a temperature range of from about 150° C. to about 400° C., and a pressure in the range of about 1 bar to 30 bar, over a fixed bed of crystalline alumino-silicate catalyst, preferably a zeolite catalyst, and most preferably a ZSM-5 zeolite catalyst. Although the zeolite catalyst is preferably used in the sodium or magnesium form, the zeolite may also be modified by ion exchange with other alkali metal cations, such as Li, K or Cs, with alkali-earth metal cations, such as Mg, Ca, Sr or Ba, or with transition metal cations, such as Ni, Mn, V, W. Other zeolite catalysts having varying pore sizes and acidities, which are synthesized by varying the alumina-to-silica ratio may be used in the second reactor 134 as will be evident to a skilled artisan. In this reactor, the alkyl bromides are oligimerized to produce a mixture of higher molecular weight hydrocarbon products and additional hydrobromic acid vapor.

The temperature at which the second reactor 134 is operated is an important parameter in determining the selectivity of the oligimerization reaction to various higher molecular weight liquid hydrocarbon products. It is preferred to operate second reactor 134 at a temperature within the range of about 150° to 400°, but more preferably within the range of about 250 C to 350 C. Temperatures above about 300° C. in the second reactor result in increased yields of light hydrocarbons, such as undesirable methane, whereas lower temperatures increase yields of heavier molecular weight hydrocarbon products. At the low end of the temperature range, methyl bromide reacting over ZSM-5 zeolite at temperatures as low as 150° C. significant methyl bromide conversion on the order of 20% is noted, with a high selectivity towards $C_5+$ products. Notably, in the case of alkyl bromides reacting over the preferred ZSM-5 zeolite catalyst, cyclization reactions occur such that the $C_7+$ fractions produced contain a high percentage of substituted aromatics. At increasing temperatures approaching 300° C., methyl bromide conversion increases towards 90% or greater, however selectivity towards $C_5+$ products decreases and selectivity towards lighter products, particularly undesirable methane, increases. Surprisingly, very little ethane or $C_2$-$C_4$ olefin compounds are produced. At temperatures above about 425° C. almost complete conversion of methyl bromide to methane occurs. As a byproduct of the reaction, a small amount of carbon will build up on the catalyst over time during operation, causing a decline in catalyst activity over a range of several hundred hours, depending on the reaction conditions. It is believed that higher reaction temperatures favor the formation of carbon and hence rate of deactivation of the catalyst. Conversely, operation at the lower end of the temperature range may promote coking, likely to the reduced rate of desorption of hydrocarbon products. Hence, operating temperatures within the range of about 150° C. to 400° C. but more preferably in the range of about 250° C. to 350° C. in the second reactor 134 balance increased selectivity towards the desired products and lower rates of deactivation due to carbon formation, against higher conversion per pass, which minimizes the quantity of catalyst, recycle rates and equipment size required.

The catalyst may be periodically regenerated in situ, by isolating reactor 134 from the normal process flow, purging with an inert gas via line 170 at a pressure in the range of about 1 bar to about 5 bar and an elevated temperature in the range of 400° C. to 600° C. to remove unreacted material adsorbed on the catalyst insofar as is practical, and then subsequently oxidizing the deposited carbon to $CO_2$ by addition of air via line 170 to reactor 134 at a pressure in the range of about 1 bar to about 5 bar and an elevated temperature in the range of 400° C. to 600° C. Carbon dioxide and residual air are vented from reactor 134 via line 175 during the regeneration period.

The effluent which comprises the higher molecular weight hydrocarbon products and hydrobromic acid is withdrawn from the second reactor 134 via line 135, cooled to a temperature in the range of 0° C. to 100° C. in exchanger 136, and combined with vapor effluent in line 112 from hydrocarbon stripper 147. The mixture is then passed to a scrubber 138 and contacted with a stripped, recirculated water that is transported to scrubber 138 in line 164 by any suitable means, such as pump 143, and is cooled to a temperature in the range of 0° C. to 50° C. in heat exchanger 155. Any liquid hydrocarbon product condensed in scrubber 138 may be skimmed and withdrawn as stream 137 and added to liquid hydrocarbon product 154. Hydrobromic acid is dissolved in scrubber 138 in the aqueous solution which is removed from the scrubber 138 via line 144, and passed to hydrocarbon stripper 147 wherein residual hydrocarbons dissolved in the aqueous solution are stripped-out by contact with feed gas 111. The stripped aqueous phase effluent from hydrocarbon stripper 147 is cooled to a temperature in the range of 0° C. to 50° C. in heat exchanger 146 and then passed via line 165 to absorber 148 in which residual bromine is recovered from vent stream 167.

The residual vapor phase containing the higher molecular weight hydrocarbon products is removed as effluent from the scrubber 138 and forwarded to dehydrator 150 to remove substantially all water from the gas stream. The water is then removed from the dehydrator 150 via line 153. The dried gas stream containing the higher molecular weight hydrocarbon products is further passed via line 151 to product recovery unit 152 to recover $C_3$ and $C_4$ as desired, but primarily the $C_5+$ fraction as a liquid product in line 154. Any conventional method of dehydration and liquids recovery such as solid-bed dessicant adsorption followed by, for example, refrigerated condensation, cryogenic expansion, or circulating absorption oil, as used to process natural gas or refinery gas streams, as known to a skilled artisan, may be employed in the implementation of this invention. The residual vapor effluent from product recovery unit 152 is then split into a purge stream 157 that may be utilized as fuel for the process and a recycled residual vapor which is compressed via compressor 158. The recycled residual vapor discharged from compressor 158 is split into two fractions. A first fraction that is equal to at least 2.5 times the feed gas volume is transported via line 162, combined with the liquid bromine conveyed in line 125 and passed to heat exchanger 126 wherein the liquid bromine is vaporized and fed into first reactor 130. The second fraction which is drawn off line 162 via line 163 and is regulated by control valve 160, at a rate sufficient to dilute the alkyl bromide concentration to reactor 134 and absorb the heat of reaction such that reactor 134 is maintained at the selected operating temperature, preferably in the range of 250° C. to 350° C. in order to optimize conversion vs. selectivity and to minimize the rate of catalyst deactivation due to the deposition of carbon. Thus, the dilution provided by the recycled vapor effluent permits selectivity of bromination in the first reactor 130 to be controlled in addition to moderating the temperature in second reactor 134.

Oxygen or $O_2$-enriched air 110 is delivered via blower or compressor 113 at a pressure in the range of about ambient to about 5 bar to bromine stripper 114 to strip residual bromine from water which leaves stripper 114 via line 164 and is divided into two portions. The first portion of the stripped water is recycled via line 164, cooled in heat exchanger 155 to a temperature in the range of about 20° C. to about 50° C., and maintained at a pressure sufficient to enter scrubber 138 by any suitable means, such as pump 143. The portion of water that is recycled is selected such that the hydrobromic acid solution effluent removed from scrubber 138 via line 144 has a concentration in the range from about 10% to about 50% by weight hydrobromic acid, but more preferably in the range of about 30% to about 48% by weight to minimize the amount of water which must be vaporized in exchanger 141 and preheater 119. A second portion of water from stripper 114 is removed from line 164 and the process via line 156.

The dissolved hydrobromic acid that is contained in the aqueous solution effluent from scrubber 148 is transported via line 149 and is combined with the oxygen or $O_2$-enriched air leaving bromine stripper 114 in line 115. The combined aqueous solution effluent and oxygen or $O_2$-enriched air is passed to a first side of heat exchanger 141 and through preheater 119 wherein the mixture is preheated to a temperature in the range of about 100° C. to about 600° C. and most preferably in the range of about 120° C. to about 180° C. and passed to third reactor 117 that contains a metal bromide salt. The preferred metal of the bromide salt is Cu(II), Zn(II) or Fe(III) although Co(II), Ni(II), Mn(II) or other transition-metals which form oxidizable bromide salts can be used. Alternatively, alkaline-earth metals which also form oxidizable bromide salts, such as Ca (II) or Mg(II) could be used. The metal bromide salt in the oxidation reactor 117 can be utilized as a concentrated aqueous solution or preferably, the concentrated aqueous salt may be imbibed into a porous, high surface area, acid resistant inert support such as a silica gel. The oxidation reactor 117 operates at a pressure in the range of about ambient to about 5 bar and at a temperature in the range of about 100° C. to 600° C., but most preferably in the range of about 120° C. to 180° C.; therein, the metal bromide is oxidized by oxygen, yielding elemental bromine and metal hydroxide or metal oxy-bromide species or, metal oxides in the case of the supported metal bromide salt operated at higher temperatures and lower pressures at which water may primarily exist as a vapor. In either case, the hydrobromic acid reacts with the metal hydroxide, metal oxy-bromide or metal oxide species and is neutralized, restoring the metal bromide salt and yielding water. Thus, the overall reaction results in the net oxidation of hydrobromic acid produced in first reactor 130 and second reactor 134 to elemental bromine and steam, catalyzed by the metal bromide/metal hydroxide or metal oxide operating in a catalytic cycle. In the case of the metal bromide being Cu(II)Br$_2$ in an aqueous solution and operated in a pressure and temperature range in which water may exist as a liquid the reactions are believed to be:

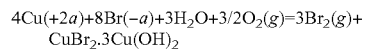

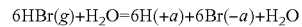

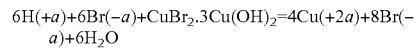

In the case of the metal bromide being Cr(II)Br$_2$ supported on an inert support and operated at higher temperature and lower pressure conditions at which water primarily exists as a vapor, the reactions are believed to be:

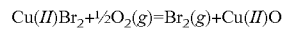

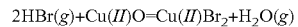

The elemental bromine and water and any residual oxygen or nitrogen (if enriched air is utilized as the oxidant) leaving as vapor from the outlet of third reactor 117, are cooled in the second side of exchanger 141 and condenser 120 to a temperature in the range of about 0° C. to about 70° C. wherein the bromine and water are condensed and passed to three-phase separator 122. In three-phase separator 122, since liquid water has a limited solubility for bromine, on the order of about 3% by weight, any additional bromine which is condensed forms a separate, denser liquid bromine phase. The liquid bromine phase, however, has a notably lower solubility for water, on the order of less than 0.1%. Thus, a substantially dry bromine vapor can be easily obtained by condensing liquid bromine and water, decanting water by simple physical separation and subsequently re-vaporizing liquid bromine.

Liquid bromine is pumped from three-phase separator 122 via pump 124 to a pressure sufficient to mix with vapor stream 162. Thus the bromine is recovered and recycled within the process. The residual enriched air or oxygen and any bromine vapor which is not condensed exits three-phase separator 122 and is passed via line 123 to bromine scrubber 148, wherein residual bromine is recovered by dissolution into hydrobromic acid solution stream conveyed to scrubber 148 via line 165. Water is removed from the three-phase separator 122 via line 129 and passed to stripper 114.

The following examples demonstrate the practice and utility of the present invention, but are not to be construed as limiting the scope thereof.

EXAMPLE 1

Various mixtures of dry bromine and methane are reacted homogeneously at temperatures in the range of 459° C. to 491° C. at a Gas Hourly Space Velocity (GHSV which is defined as the gas flow rate in standard liters per hour divided by the gross reactor catalyst-bed volume, including catalyst-bed porosity, in liters) of approximately 7200 hr$^{-1}$. The results of this example indicate that for molar ratios of methane to bromine greater than 4.5:1 selectivity to methyl bromide is in the range of 90 to 95%, with near-complete conversion of bromine.

EXAMPLE 2

Figure 7:
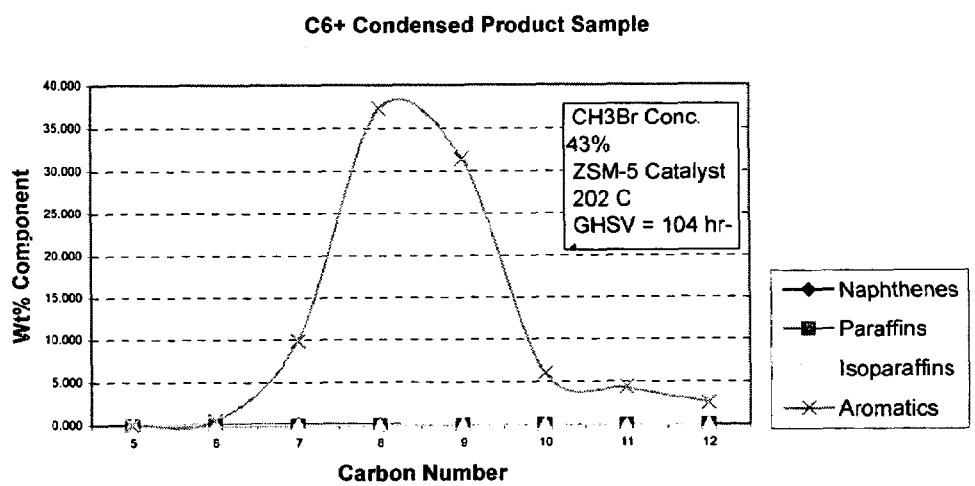
FIG. 7 is a graph of a Paraffinic Olefinic Napthenic and Aromatic (PONA) analysis of a typical condensed product sample of the process of the present invention.
Figure 8:
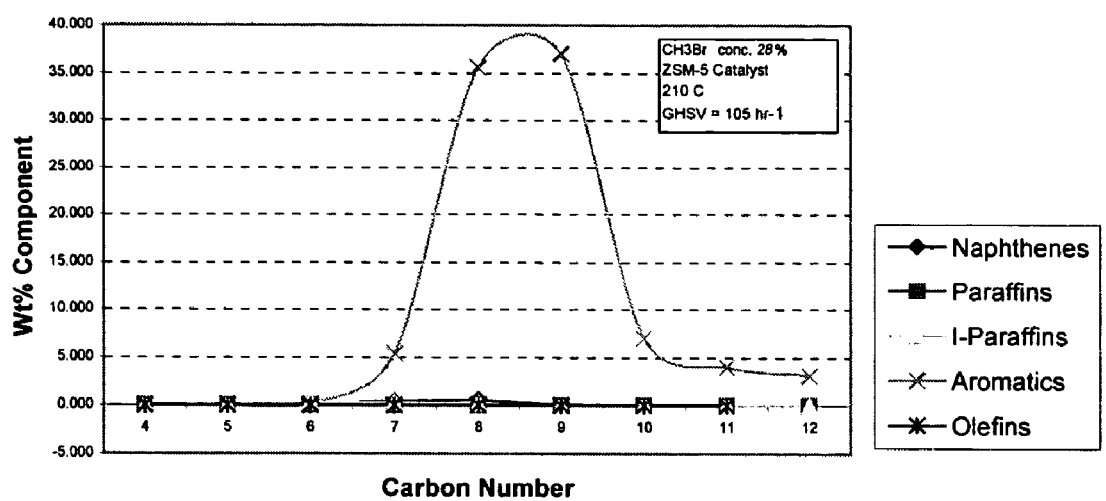
FIG. 8 is a graph of a PONA analysis of another typical condensed product sample of the present invention.

FIG. 7 and FIG. 8 illustrate two exemplary PONA analyses of two C$_6$+ liquid product samples that are recovered during two test runs with methyl bromide and methane reacting over ZSM-5 zeolite catalyst. These analyses show the substantially aromatic content of the C$_6$+ fractions produced.

EXAMPLE 3

Figure 4:
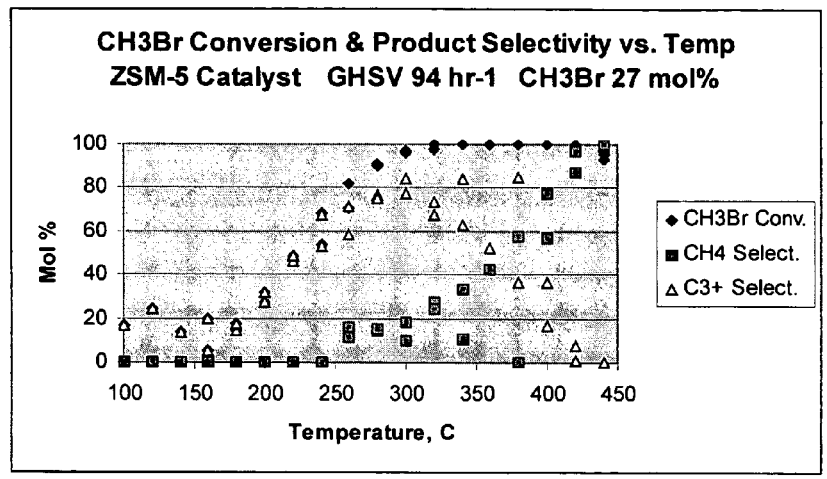
FIG. 4 is a graph of methyl bromide conversion and product selectivity for the oligimerization reaction of the process of the present invention as a function of temperature.

Methyl bromide is reacted over a ZSM-5 zeolite catalyst at a Gas Hourly Space Velocity (GHSV) of approximately 94 hr$^{-1}$ over a range of temperatures from about 100° C. to about 460° C. at approximately 2 bar pressure. As illustrated in FIG. 4, which is a graph of methyl bromide conversion and product selectivity for the oligimerization reaction as a function of temperature, methyl bromide conversion increases rapidly in the range of about 200° C. to about 350° C. Lower temperatures in the range of about 100° C. to about 250° C. favor selectivity towards higher molecular weight products however conversion is low. Higher temperatures in the range of about 250° C. to about 350° C. show higher conversions in the range of 50% to near 100%, however increasing selectivity to lower molecular weight products, in particular undesirable methane is observed. At higher temperatures above 350° C. selectivity to methane rapidly increases. At about 450° C., almost complete conversion to methane occurs.

EXAMPLE 4

Figure 5:
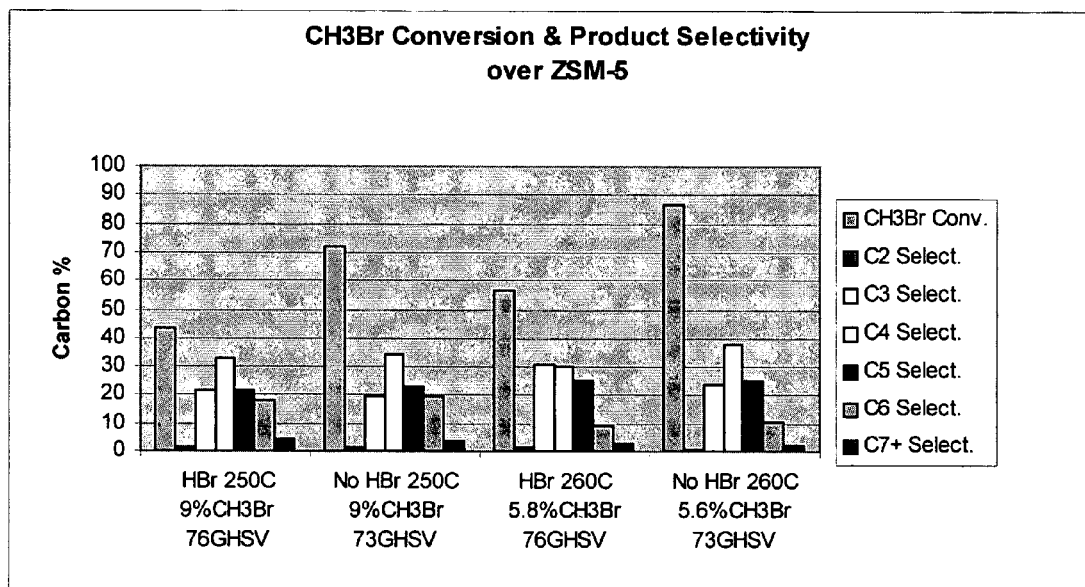
FIG. 5 is a graph comparing conversion and selectivity for the example of methyl bromide, dry hydrobromic acid and methane versus only methyl bromide plus methane.

Methyl bromide, hydrogen bromide and methane are reacted over a ZSM-5 zeolite catalyst at approximately 2 bar pressure at about 250° C. and also at about 260° C. at a GHSV of approximately 76 hr$^{-1}$. Comparison tests utilizing a mixture of only methyl bromide and methane without hydrogen bromide over the same ZSM-5 catalyst at approximately the same pressure at about 250° C. and at about 260° C. at a GHSV of approximately 73 hr$^{-1}$ were also run. FIG. 5, which is a graph that illustrates the comparative conversions and selectivities of several example test runs, shows only a very minor effect due to the presence of HBr on product selectivities. Because hydrobromic acid has only a minor effect on conversion and selectivity, it is not necessary to remove the hydrobromic acid generated in the bromination reaction step prior to the conversion reaction of the alkyl bromides, in which additional hydrobromic acid is formed in any case. Thus, the process can be substantially simplified.

EXAMPLE 5

Figure 6:
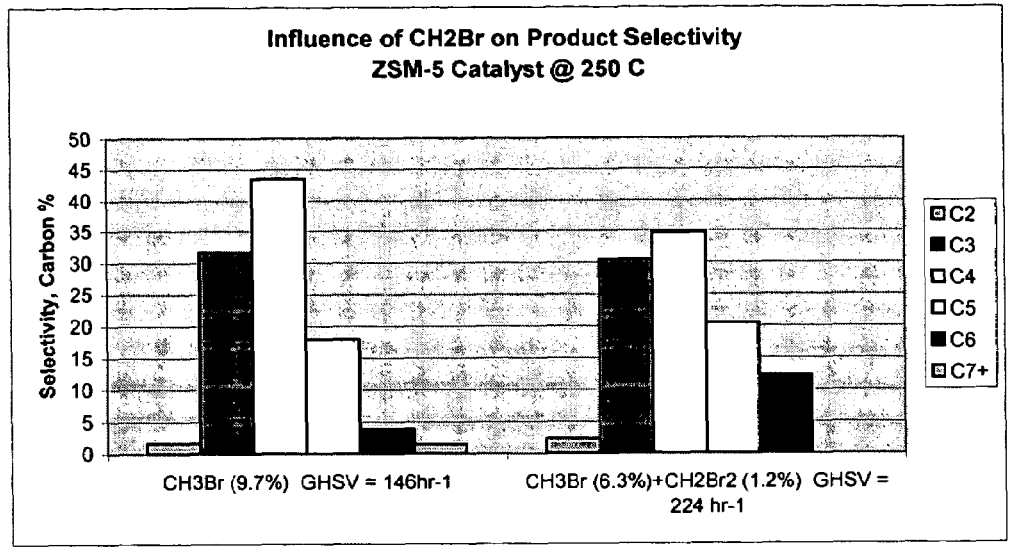
FIG. 6 is a graph of product selectivity from reaction of methyl bromide and dibromomethane vs. product selectivity from reaction of methyl bromide only.

Methyl bromide is reacted over a ZSM-5 zeolite catalyst at 230° C. Dibromomethane is added to the reactor. FIG. 6, which is a graph of product selectivity, indicates that reaction of methyl bromide and dibromomethane results in a shift in selectivity towards $C_5+$ products versus. methyl bromide alone. Thus, these results demonstrate that dibromomethane is also reactive and therefore very high selectivity to bromomethane in the bromination step is not required in the process of the present invention.

EXAMPLE 6

A mixture of 12.1 mol % methyl bromide and 2.8 mol % propyl bromide in methane are reacted over a ZSM-5 zeolite catalyst at 295 C and a GHSV of approximately 260 hr$^{-1}$. A methyl bromide conversion of approximately 86% and a propyl bromide conversion of approximately 98% is observed.

Thus, in accordance with all embodiments of the present invention, the metal bromide/metal hydroxide, metal oxy-bromide or metal oxide operates in a catalytic cycle allowing bromine to be easily recycled within the process. The metal bromide is readily oxidized by oxygen or air either in the aqueous phase or the vapor phase at temperatures in the range of about 100° C. to about 600° C. and most preferably in the range of about 120° C. to 180° C. to yield elemental bromine vapor and metal hydroxide, metal oxy-bromide or metal oxide. Operation at temperatures below about 180° C. is advantageous, thereby allowing the use of low-cost corrosion-resistant fluoropolymer-lined equipment. Hydrobromic acid is neutralized by reaction with the metal hydroxide or metal oxide yielding steam and the metal bromide.

The elemental bromine vapor and steam are condensed and easily separated in the liquid phase by simple physical separation, yielding substantially dry bromine. The absence of significant water allows selective brormlination of alkanes, without production of $CO_2$ and the subsequent efficient and selective oligimerization and cyclization reactions of alkyl bromides to primarily propane and heavier products, the $C_5+$ fraction of which contains substantial branched alkanes and substituted aromatics. Byproduct hydrobromic acid vapor from the bromination and oligimerization reaction are readily dissolved into an aqueous phase and neutralized by the metal hydroxide or metal oxide species resulting from oxidation of the metal bromide.

The process of the present invention is less expensive than conventional process since it operates at low pressures in the range of about 1 bar to about 30 bar and at relatively low temperatures in the range of about 20° C. to about 600° C. for the gas phase, and preferably about 20° C. to about 180° C. for the liquid phase. These operating conditions permit the use of less expensive equipment of relatively simple design that are constructed from readily available metal alloys for the gas phase and polymer-lined vessels, piping and pumps for the liquid phase. The process of the present invention is also more efficient because less energy is required for operation and the production of excessive carbon dioxide as an unwanted byproduct is minimized. The process is capable of directly producing a mixed hydrocarbon product containing various molecular-weight components in the liquefied petroleum gas (LPG) and motor gasoline fuels range that have substantial aromatic content thereby significantly increasing the octane value of the gasoline-range fuel components.

While the foregoing preferred embodiments of the invention have been described and shown, it is understood that the alternatives and modifications, such as those suggested and others, may be made thereto and fall within the scope of the invention.

I claim:

1. A process for converting gaseous alkanes to liquid hydrocarbons comprising:
   reacting a gaseous feed having lower molecular weight alkanes with bromine vapor to form alkyl bromides and hydrobromic acid; and
   reacting said alkyl bromides in the presence of said hydrobromic acid and a catalyst consisting essentially of a synthetic crystalline alumino-silicate catalyst and at a temperature sufficient to form higher molecular weight hydrocarbons and additional hydrobromic acid.

2. The process of claim 1 wherein said bromine vapor is substantially dry, thereby avoiding the formation of significant carbon dioxide along with said alkyl bromides.

3. The process of claim 1 wherein said gaseous feed is natural gas.

4. The process of claim 3 wherein said natural gas is treated to remove substantially all of the carbon dioxide and sulfur compounds therefrom prior to reacting with said bromine vapor.

5. The process of claim 1 wherein said temperature is from about 150° C. to about 400° C.

6. The process of claim 5 wherein said temperature is from about 250° C. to about 350° C.

7. The process of claim 1 wherein said crystalline alumino-silicate catalyst is a zeolite catalyst.

8. The process of claim 7 wherein said zeolite catalyst is a ZSM-5 zeolite catalyst and said higher molecular weight hydrocarbons contain a $C_7+$ fraction that is composed primarily of substituted aromatics.

9. The process of claim 8 wherein said ZSM-5 zeolite catalyst is modified with at least one modifying cation selected from hydrogen and Group IA alkaline metals, or Group IIA alkaline earth metals.

10. The process of claim 9 wherein said ZSM-5 zeolite catalyst is modified by ion exchange with at least one cation selected from hydrogen, sodium, potassium, cesium, magnesium, calcium or barium.

11. The process of claim 1 wherein said bromine vapor is produced by oxidizing an aqueous metal bromide salt solution, the metal of said metal bromide salt being selected from Cu, Zn, Fe, Go, Ni, Mn, Ca, or Mg.

12. The process of claim 1 wherein said bromine vapor is produced by oxidizing a metal bromide salt contained on a porous support, the metal of said metal bromide salt being selected from the group Cu, Zn, Fe, Go, Ni, Mn, Ca, or Mg.

13. The process of claim 1 wherein said higher molecular weight hydrocarbons contains a $C_3$, $C_4$ and $C_5+$ fractbns in admixture with excess lower alkanes, the process further comprising:
dehydrating said higher molecular weight hydrocarbons to a dew point of about −20° C. or less so as to recover said $C_5+$ fractions as a liquid.

14. The process of claim 13 further comprising:
mixing at least a portion of said $C_3$ and $C_4$ fractions with said alkyl bromides and said hydrobromic acid prior to the step of reacting over said synthetic crystalline alumino-silicate catalyst.

15. The process according to claim 1 wherein said step of reacting said gaseous feed with said bromine vapor occurs in a first reactor and said step of reacting said alkyl bromides occurs in a second reactor.

16. The process of claim 1 wherein each of said hydrobromic acid and said additional hydrobromic acid is a vapor.

17. A process for converting gaseous lower molecular weight alkanes to liquid hydrocarbons comprising:
reacting a gaseous feed containing lower molecular weight alkanes with bromine vapor to form alkyl bromides and hydrobromic acid:
reacting said alkyl bromides in the presence of a synthetic crystalline alumino-silicate catalyst and hydrobromic acid to form higher molecular weight hydrocarbons and additional hydrobromic acid; and
contacting said hydrobromic acid, said additional hydrobromic acid, and said higher molecular weight hydrocarbons wDth water to remove said hydrobromic acid and additional hydrobromic acid from said higher molecular weight hydrocarbons.

18. The process of claim 17 wherein said water is an aqueous solution and said step of contacting comprises:
removing said hydrobromic acid and said additional hydrobromic acid from said higher molecular weight hydrocarbons by neutralization reaction with said aqueous solution containing reaction products obtained by oxidizing an aqueous solution containing a metal bromide salt, the metal of said metal bromide salt being selected from Cu, Zn, Fe, Go, Ni, Mn, Ca or Mg bromide.

19. The process of claim 17 wherein said step of contacting comprises:
removing said hydrobromic acid and said additional hydrobromic acid from said higher molecular weight hydrocarbons by dissolution into said water forming a hydrobromic acid solution, said hydrobromic acid solution being neutralized by reaction with an aqueous solution containing a metal hydroxide obtained by oxidizing an aqueous metal bromide salt solution with oxygen, the metal of said metal bromide salt being selected from Cu, Zn, Fe, Go, Ni, Mn, Ca or Mg.

20. The process of claim 17 wherein said step of contacting comprises removing said hydrobromic acid and said additional hydrobromic acid from said higher molecular weight hydrocarbons by dissolution into said water forming a hydrobromic acid solution, said process further comprising:
vaporizing said hydrobromic acid solution and reacting said vaporized hydrobromic acid solution with a metal oxide, said metal oxide being obtained by oxidizing a metal bromide salt contained on a porous support, the metal of said metal bromide salt being selected from the group Cu, Zn, Fe, Go, Ni, Mn, Ca or Mg.

21. The process of claim 17 further comprising:
converting said hydrobromic acid and said additional hydrobromic acid to bromine.

22. The process of claim 21 further comprising:
dehydrating said higher molecular weight hydrocarbons.

23. The process of claim 21 further comprising:
recycling said bromine that is converted from said hydrobromic acid and additional hydrobromic acid to said step of reacting with said gaseous feed, said bromine being recycled as a vapor.

24. The process according to claim 17 wherein said step of reacting said gaseous feed with said bromine vapor occurs in a first reactor and said step of reacting said alkyl bromides occurs in a second reactor.

25. The process of claim 17 wherein each of said hydrobromic acid and said additional hydrobromic acid is a vapor.

26. A process for converting gaseous alkanes to liquid hydrocarbons comprising:
introducing a mixture comprising lower molecular weight gaseous alkanes and bromine vapor to a first reactor;
withdrawing alkyl bromides and hydrobromic acid from said first reactor;
introducing said alkyl bromides and said hydrobromic acid into a second reactor containing a synthetic crystalline alumino-silicate catalyst; and
withdrawing an effluent comprising higher molecular weight hydrocarbons and said hydrobromic acid from said second reactor.

27. The process of claim 26 wherein said higher molecular weight hydrocarbons contains $C_5+$ fractions.

28. The process of claim 26 wherein said hydrobromic acid is a vapor.

* * * * *

UNITED STATES PATENT AND TRADEMARK OFFICE
CERTIFICATE OF CORRECTION

PATENT NO. : 7,244,867 B2  Page 1 of 1
APPLICATION NO. : 10/826885
DATED : July 17, 2007
INVENTOR(S) : John J. Waycuilis It is certified that error appears in the above-identified patent and that said Letters Patent is hereby corrected as shown below:

Column 6, line 28, after "41", insert: --by any suitable means, such as by pump 42--.

Column 9, line 20, after "bed", insert: --133--.

Column 10, line 44, after "forwarded", insert: --via line 139--.

Column 12, line 18, after "are", insert: --transported via line 127 and--.

Column 14, line 12, delete "brormlination" and replace with: --bromination--.

Column 15, Claim 11, line 20, delete "Go" and replace with: --Co--.

Column 15, Claim 12, line 24, delete "Go" and replace with: --Co--.

Column 15, Claim 13, line 26, delete "fractbns" and replace with: --fractions--.

Column 15, Claim 17, line 47, delete ":" and replace with: --;--.

Column 15, Claim 17, line 54, delete "wDth" and replace with: --with--.

Column 16, Claim 18, line 3, delete "Go" and replace with: --Co--.

Column 16, Claim 19, line 15, delete "Go" and replace with: --Co--.

Column 16, Claim 20, line 27, delete "Go" and replace with: --Co--.

Signed and Sealed this

Twenty-seventh Day of May, 2008

JON W. DUDAS
*Director of the United States Patent and Trademark Office*